:

US008668913B2

(12) United States Patent
Ahmad et al.

(10) Patent No.: US 8,668,913 B2
(45) Date of Patent: Mar. 11, 2014

(54) COMPLEMENTARY PERSONAL LUBRICANT COMPOSITIONS

(75) Inventors: Nawaz Ahmad, Monmouth Junction, NJ (US); Cheng-Ji Cui, Pennington, NJ (US); Bryant Ison, Lawrenceville, NJ (US)

(73) Assignee: Personal Products Company, Skillman, NJ (US)

( * ) Notice: Subject to any disclaimer, the term of this patent is extended or adjusted under 35 U.S.C. 154(b) by 541 days.

(21) Appl. No.: 11/842,487

(22) Filed: Aug. 21, 2007

(65) Prior Publication Data

US 2008/0193492 A1 Aug. 14, 2008

Related U.S. Application Data

(60) Provisional application No. 60/889,062, filed on Feb. 9, 2007.

(51) Int. Cl.
*A61K 8/02* (2006.01)
*A61K 31/74* (2006.01)

(52) U.S. Cl.
USPC ........................................ 424/401; 424/78.02

(58) Field of Classification Search
USPC .......................................................... 424/401
See application file for complete search history.

(56) References Cited

U.S. PATENT DOCUMENTS

| 4,310,488 | A |   | 1/1982 | Rahm et al. |         |
|-----------|---|---|--------|-------------|---------|
| 4,869,723 | A | * | 9/1989 | Harmon      | 604/349 |
| 5,208,031 | A |   | 5/1993 | Kelly       |         |
| 5,316,398 | A |   | 5/1994 | Chandaria et al. |    |
| 6,039,951 | A |   | 3/2000 | Bjeldbak    |         |
| 6,581,775 | B1|   | 6/2003 | Hagopian    |         |
| 6,641,825 | B2|   | 11/2003| Scholz et al. |       |
| 6,793,937 | B2| * | 9/2004 | Quong       | 424/489 |
| 7,005,408 | B2|   | 2/2006 | Ahmad et al. |        |
| 7,166,137 | B2|   | 1/2007 | Narasimhan et al. |   |
| 7,405,186 | B2| * | 7/2008 | Harrison    | 508/579 |
| 7,709,428 | B2|   | 5/2010 | Chuah et al. |        |
| 2002/0187165 | A1 | | 12/2002 | Harbeck    |         |
| 2003/0211161 | A1 | | 11/2003 | Ahmad et al. |      |
| 2003/0232090 | A1 | * | 12/2003 | Ahmad et al. | 424/488 |
| 2005/0042248 | A1 | * | 2/2005 | Ahmad et al. | 424/423 |
| 2005/0244520 | A1 | | 11/2005 | Thompson et al. |   |
| 2006/0188528 | A1 | * | 8/2006 | Chuah et al. | 424/400 |

FOREIGN PATENT DOCUMENTS

| EP | 0 644 129 A | 3/1995 |
| ES | 2 074 030 | 8/1995 |
| JP | 2 311 408 | 12/1990 |
| WO | WO 02/45573 A2 | 6/2002 |

OTHER PUBLICATIONS

Merriam-Webster Online Dictionary, "Menthol" definition; available at: http://www.merriam-webster.com/dictionary/menthol.*
Schwartz et al. The Great Sex Weekend. Berkley Publishing Co. (1997), p. 111.*
Morrissey. 52 Recipes to Heat Up Your Sex Life. Marlowe & Company (2006), p. 179-180.*
Estronaut (www.estronaut.com) (1999).*
Estronaut (www.estronaut.com)(1999).*
Anonymous, "Cambridge Chemistry Set", Jan. 24, 2007 (XP002482987), retrieved from the internet on Jun. 4, 2008: URL:http://web.archive.org/web/20070124212213/http://www.otherlandtoys.co.uk/cambridge-chemistry-set-p-1759.html.
Female condom becomes available nationwide, contraception report, vol. 5, No. 6, Jan. 1995 (XP002679461).
Smith, Anthony MA, et al.; Does additional lubrication affect condom slippage and breakage?; Int'l Journ. of std and aids, royal society of medicine services; vol. 9, No. 6, Jun. 1, 1998; pp. 330-335 (XP008153277).
Yang, R.; Zhang W.; Zhang Z.; Sanitary paper towel sprayed with three liq. Meds—for use before and after sexual intercourse to prevent diseases of male and female genitalia; Thomson Scientific; Mar. 13, 1991 (XP002679462).
He, C.; Lubricant for application to glans penis—made from dried toad venom and Chinese plants and used for treatment of premature ejaculation; Feb. 27, 1991 (XP002679464).

* cited by examiner

*Primary Examiner* — Daniel Sullivan
*Assistant Examiner* — Melissa Javier

(57) ABSTRACT

This invention relates to novel compositions and methods of use by which the compositions of this invention are applied topically to one or more body parts of at least two individuals who bring said body parts into contact with the other individual and, when said body parts come into contact with each other, permit the formulations to interact and thereby achieve an unexpected sensation to each individual.

16 Claims, No Drawings

COMPLEMENTARY PERSONAL LUBRICANT COMPOSITIONS

This application claims the benefit of provisional application Ser. No. 60/889,062 filed on Feb. 9, 2007.

FIELD OF THE INVENTION

This invention relates to personal lubricant compositions and methods of using such compositions in conjunction with each other by distinct individuals to create new and/or intensified sensations in relation to interpersonal use.

BACKGROUND OF THE INVENTION

Personal lubricant have been sold for decades for the purposes of treating vaginal dryness, for promoting ease of engaging in intimate physical relations and for lubricating diagnostic devices for insertion into body orifices. However, for the last quarter century personal lubricants have achieved an entirely new role in enhancing and making more pleasurable sexual experiences. Personal lubricants have become perceived as a great means to help set the mood for intimate experiences and enhance intimacy. Current personal lubricants may be used by either or both the partners to achieve this goal.

New and more recent additions to this product line are safe, non-irritating warming products that generate warmth when they come into contact with moisture. Examples of such warming personal lubricants are set forth in, for example, U.S. Pat. No. 7,005,408 as well as copending patent applications U.S. Ser. Nos. 10/390,511, 10/389,871, 10/696,939, 10/697,353, 10/697,838, 10/847,082 and 10/847,083, which are hereby incorporated herein by reference.

As intimacy enhancement gains increased focus, substantial number of lubricant products are appearing on the market that work by increasing sensitivity in both males and females by imparting tingling, cooling, numbing or additional unique sensation.

U.S. Pat. No. 6,641,825 B2 of Scholz et al. entitled "Skin Cleansing Gel Having a Heating Effect" describes compositions containing at least 5% by weight of dispersed water-soluble salts with a negative enthalpy of solution, which will release heat upon mixing with water. The compositions also contain anionic, zwitterionic and nonionic surfactants. Such compositions, however, are unsuitable for personal lubricant use as they would be irritating to the delicate mucous membranes of the body.

Japanese Patent Application Number 2-311408, of Akiyama et al., entitled "Gelatinous Compositions for the Skin" sets forth compositions that may contain 0-20% water; solvents such as lower alcohols such as ethanol, isopropanol, propyl alcohol, or organic ethers such as ethyl carbitol, ethyl cellulosolve, chloroform, isopropyl myristate and isopropyl palmitate; and a polyhydric alcohol such as propylene glycol, glycerin, diglycerin and dipropylene glycol. These compositions warm by interacting with water but may have the potential for irritation of mucosal membranes.

Spanish Patent Number ES2, 074,030 by Manuel Roig Carreras et al., entitled "Self-heating Vehicle Compositions That Can Be Used in Topical Treatments" discusses liquid or semisolid compositions that generate heat by means of an in situ mixing of similar amounts of an aqueous portion (W) consisting mainly of water or an aqueous gel and an organic portion (O) consisting mainly of dimethyl sulfoxide (DMSO), dimethylene glycol or polyethylene glycol. Carreras et al. describes the compositions as being contained in two isolated compartments with adjacent openings that permit simultaneous exit of two parts of self-heating compositions. The compositions of this invention may not be suitable for use as personal lubricants because the DMSO is not suitable for human use and the temperature of the compositions when combined may be too elevated to be safe and comfortable in personal lubricant applications.

The novel compositions and methods of this invention are intended to provide novel sensations to the skin of at least two individuals without being unduly irritating and which interact to provide novel or more intense sensations than each would experience absent the exposure, combination and interaction of the initially-applied compositions to each.

SUMMARY OF THE INVENTION

This invention relates to novel compositions and methods of use by which the compositions of this invention are applied topically to one or more body parts of at least two individuals who bring said body parts into contact with the other individual and, when said body parts come into contact with each other, permit the formulations to interact and thereby achieve an unexpected sensation to each individual. Such sensation may be intensified in relation to the sensation experienced from the initially-applied composition. Alternatively, the sensation experienced by each individual upon combination and interaction of the at least two compositions may be distinctly different from that experienced upon initial application of a first composition. The sensation experienced may alternatively also be an intensification of a sensation of a first composition.

DETAILED DESCRIPTION OF PREFERRED EMBODIMENTS

More particularly, this invention relates to a method of creating a sensory result on the skin or mucosa of at least two individuals comprising:

a) applying a first topical composition to the skin or mucosa of at least one first individual;

b) applying a second topical composition to the skin or mucosa of at least one second individual, said second topical composition being different from said first topical composition;

c) bringing the skin of at least one first individual to which said first composition is applied into contact with the skin or mucosa of the second individual to which said second composition is applied; whereby said first and said second topical compositions interact and result in a sensation in at least one of said individuals. Such compositions may be applied to more than two individuals.

More particularly, this invention also relates to a method of creating a sensory result on the skin or mucosa of at least two individuals comprising:

a) applying a first topical composition to the skin or mucosa of at least one first individual, said first topical composition eliciting a first sensation from said first individual;

b) applying a second topical composition to the skin or mucosa of at least one second individual, said second topical composition being different from said first topical composition and which elicits a second sensation from said second individual;

c) bringing the skin of at least one first individual to which said first composition is applied into contact with the skin or mucosa of the second individual to which said second composition is applied; whereby said first and said second topical compositions interact and result in a sensation in each individual or an intensification of said sensation in said first or said second individual. Such compositions may be applied to more than two individuals.

As used herein, the term "sensation" means an awareness due to stimulation of a sense organ. There are a number of sensations that are known to play a role in enhancing intimate and sexually-related activities. Some have been utilized in conjunction with intimate lubricant compositions in the past to deliver and enhance sexual satisfaction during intimate relationship. The sensation may be a different sensation from that generated by the first topical composition; it may be the same sensation, which is made more intense; or such new sensation may be felt only by one of the partners to which the compositions have been applied. The following are properties or sensations that can be imparted to compositions according to this invention which, when used in accordance with the methods of this invention, convey particular sensations to individuals on whose skin such compositions are placed.

Said compositions may be similar to each other, however they may differ in the proportion of one or more ingredients. Alternatively, they may be different in the type of ingredients present in each compositions. Alternatively, they may contain one or more sensates.

In addition, the compositions and methods of this invention may also include a composition in addition to said first and second compositions that may be useful in halting sensations. Such compositions may include topical analgesics such as lidocaine or benzocaine or the like.

Lubricity or Lubrication

This sensation is one of reduced friction between two surfaces and has been very successfully used in many intimate lubricant products. Lubricant products having higher lubricity helps make sexual relations more physically comfortable, thus eliminating one source of stress in a physical relationship and thereby encouraging intimacy and closeness between the participants. Lubricants or moisturizers may include water-soluble polyhydric alcohols such as propylene glycol, glycerin and polyethylene glycols and the like (others are set forth in U.S. Pat. No. 7,005,408 as well as copending patent applications U.S. Ser. Nos. 10/390,511, 10/389,871, 10/696,939, 10/697,353, 10/697,838, 10/847,082 and 10/847,083, which are hereby incorporated herein by reference.) may be used in aqueous or anhydrous compositions along with glydants like cellulose gums, polyquaterniums, polyacrylamides, polysaccharides, carbopols and acrylic acid polymers. Silicones are another class of compounds that are very lubricating and may be used to achieve this goal. In addition, other polymers may be used in the compositions and methods of this invention, such as polyquaterniums, polyacrylamides, polysaccharides and the like.

Lubricity may be measured in accordance with the test set forth in U.S. Pat. No. 5,885,591, which is hereby incorporated herein by reference.

Shear-thickening fluids such as polymers that thicken upon combination with other ingredients may be used to generate frictional or tactile sensations. For example, fluids such as corn starch solutions or dispersions or formulations thickened with high levels of polyethylene glycol distearate may thicken and may even gellify under high shear rates.

Frictional or Tactile Sensation

Frictional elements may be useful in the products of this invention to enhance the feeling of touch or tactile sensation that may be preferred by some individuals. In condoms, friction has been successfully employed by condom manufacturers by incorporating ribs and other projections of various forms, size and shape. However these condoms convey the increased sensation only to a female partner. Mechanisms that may contribute to the sensation of friction for a male individual may include the addition of microbeads that can be dispersed in a lubricant compositions. Microbeads are extremely small spheres (approximately 0.2 mm to about 1.6 mm in diameter) composed of cellulose, hydroxypropyl methylcellulose, agar, ALGIN, chitosan materials or a combination thereof, which may be obtained commercially as Primaspheres or Primasponge from Cognis Iberia, Poligon Industrial Saint Vincens, 08755 Castellbisbal, Barcelona, Spain. Addition of microbeads to the compositions of this invention is expected to convey this sensation to be experienced by both partners. Such microbeads may also be constituted such that they are dissolvable in other formulations.

The frictional or tactile sensation may be measured by various computer assisted Tactile Communication Systems specially the ones designed on Braille System by which blinds are able to read foe example TacTapad by Tactiva, 250 W Meadow Drive, Palo Alto, Calif. 94306.

Warming

Warming is a sensation that is associated with closeness and comfort and is measured by the observation of an increase in temperature. It is, therefore, a very positive feeling to bring into an intimate relationship. Warming has been successfully used in anhydrous formulations containing polyhydric alcohols (See, for example, U.S. Pat. No. 7,005,408). The warming sensation may be enhanced if it is used in combination with a non-warming lubricant. Warming and non-warming compositions of this invention may be applied separately to two intimate partners. When the two compositions are combined during the course of sexual intercourse, each partner will experience a sensation of enhanced warmth.

The degree of warming associated with the use of the compositions of applicants' invention may be measured in accordance with the procedures set forth in U.S. Pat. No. 7,005,408, which is hereby incorporated herein by reference.

Cooling

The "cooling" sensation is the opposite of warming, i.e., it is measured by an observation of a decrease in temperature. Cooling is considered an enhancement to intimate relations by some individuals. Cooling sensations may be achieved by including menthol, sorbitol, clohexanecarboxamide, N-methyl-5-methyl-2-(1-methylethyl sold under the trade name Winsense Ws-3, N,2,3-trimethyl-2-isopropyl butamide sold under the trade name Winsense SW-23 and a mixture of these sold under the trade name Winsense Extra 400 by Millenium Specialty Chemicals Inc., which is a Lyanodell Company._in the compositions of this invention. The cooling sensation may be measured by the use of cooling threshold levels experienced by human subjects. Combining the cooling sensation with another sensation generated by another composition of this invention results in a new, different sensation for both partners utilizing these compositions.

Tingling

"Tingling" is a unique sensation imparted by some chemicals such as methyl salicylate, methyl nicotinate, menthyl lactate and other chemicals. It is defined as "feeling a ringing, stinging, prickling or thrilling sensation" (Webster's Ninth New Collegiate Dictionary, Merriam-Webster, Springfield, Mass., 1987, p. 1236). Compositions that cause the tingling sensation can be used alone or with cooling or warming lubricant compositions to create a novel sensation.

Numbing

"Numbing" is the feeling characterized by the loss of sensation in a particular area of the body. Numbing may be brought about by local anesthetics such as benzocaine, novocaine, lidocaine, tetracaine, lignocaine, mepivacaine and the like. The numbing feeling may be utilized in compositions applied to a male partner in order to decrease sensitivity of the sexual organs. This can result in a prolongation of intimate physical activities.

Irritation

"Irritation" is a condition of soreness, roughness or inflammation of a body part. Irritants are entities that cause the feeling of irritation. Irritants have been included in sexual lubricant compositions for many years to convey a sensation of soreness or inflammation which may be perceived as aphrodisiac as it increases sensitivity. However, irritation may be perceived as negative or uncomfortable if used in an uncontrolled fashion. We have found that, if used at lower concentrations in accordance with the methods and compositions of this invention, irritants may create a pleasantly irritating sensation in the user. Spices such as pepper, capsicum, olive, ginger and cloves and the like and extracts thereof are some examples that may be useful in one or more of the compositions of this invention to create novel sensations in conjunction with other compositions.

Flushing

"Flushing" is the sensation created by enhanced blood flow in a body portion that can cause redness and engorgement of tissues. Engorgement of sexual organs in both females and males is an indication of arousal in both females and males. Certain natural products, such as pepper, chili pepper, ginger and the like may cause such a sensation.

As set forth above, the compositions of this invention are preferably applied in such a way that at least one composition (Composition A) is topically applied to a body part (such as the skin or mucosa) of a first sexual partner and at least one second composition (Composition B) is topically applied to a body part (such as the skin or mucosa) of a second sexual partner. After such application, the partners bring into intimate contact their respective body parts to which the compositions have been applied. The compositions of this invention are designed in such a way as to convey a first sensation when used alone by each partner and a separate, distinct, possibly intensified, sensation in at least one of the partners when body parts containing Composition A and Composition B are brought into intimate contact with each other.

When the two partners bring their body parts to which the compositions are applied into contact with each other, the compositions mix and interact with each other. The result is the generation of a new sensation or enhancement of the major or the target sensation that is felt or perceived by both partners.

Preferably, the methods of this invention encourage couples in engaging in foreplay, including having one partner applying said first composition to a second partner and said second partner applying said second composition to said first partner. Said method encourages the partners to engage in interactions such as foreplay prior to intercourse. In addition, the compositions of this invention may be utilized in conjunction with condoms and other devices useful in the practice of intimate sexual relations. For example, a male may apply a first composition to a condom, a female may apply a second composition to her perineal area and they may bring said condom into contact with said female's perineal area in order to bring the compositions into contact with each other to result in a sensation for both partners.

The invention is illustrated by the following examples.

EXAMPLE 1

Warming Sensation

A first composition as set forth below may be applied to the skin of a first intimate partner. It should convey a feeling of warmth upon application and exposure to ambient moisture in the skin of the first intimate partner. A second composition as set forth below may be applied to the skin of a second partner. This composition is a personal, or sexual, lubricant composition having a high lubricity. The two individuals may bring the skin to which the first and second compositions are applied into contact. Due to the presence of water in the second composition, the combination of the first and second compositions are expected to generate a large increase in temperature.

Such large increase in temperature may be predicted in accordance with the following procedure: 20 ml of each of the ingredients in the First Composition below and the entirety of the First Composition are mixed with 20 ml of the Second Composition. The temperature of the individual ingredient or the First Composition and that of the Second Composition are recorded before the Second Composition is added to the product. After the addition of the Second Composition, the mixture is mixed for two minutes and the actual temperature is recorded. The results of carrying out such a test using the compositions set forth below are as follows:

| First Composition (Warming) | |
|---|---|
| Ingredient | % w/w |
| Propylene Glycol | 25.00 |
| Polyethylene Glycol 400 | 75.00 |
| Total | 100.00 |

| Second Composition (Lubricating) | |
|---|---|
| Ingredient | % w/w |
| Polyol | 15.00 |
| Hydroxyalkyl cellulose | 0.75 |
| Preservative | 0.20 |
| Emulsifier | 0.10 |
| Antioxidant | 0.01 |
| Water | 83.94 |
| Total | 100.00 |

Warming Results:

Temperature of A: 73° F.

Temperature of B: 71.7° F.

Temperature upon combination: 91.5° F.

Temperature increase upon combination: 19.8° F.

EXAMPLE 2

Warming Sensation

First and second compositions as set forth below may be first applied to separate partners and then the skin of both partners to which the compositions may be applied were brought into direct contact. This is expected to result in an increased temperature that would be felt by both individuals.

| First Composition (Warming) | |
| --- | --- |
| Ingredient | % w/w |
| Propylene Glycol | 25.00 |
| Polyethylene Glycol 400 | 75.00 |
| Total | 100.00 |

| Second Composition (Lubricating) | |
| --- | --- |
| Ingredient | % w/w |
| Sorbitol Solution | 20.00 |
| Hydroxyethylcellulose | 0.20 to 0.40 |
| Water | 79.6 to 79.8 |
| Total | 100.00 |

Warming Results:

Temperature of First Composition: 71.6° F.

Temperature of Second Composition: 73.2° F.

Temperature on Mixing: 92.4° F.

Temperature increase upon combination: 20° F.

EXAMPLE 3

Warming and Tingling Sensation

First and second compositions set forth below may be applied to a first and a second partner as set forth in Examples 1 and 2 above.

| First Composition (Warming) | |
| --- | --- |
| Ingredient | % w/w |
| Propylene Glycol | 25.00 |
| Polyethylene Glycol 400 | 75.00 |
| Total | 100.00 |

| Second Composition (Tingling) | |
| --- | --- |
| Ingredient | % w/w |
| Polyol | 35.00 |
| Cooling Ingredient 1 | 0.05 |
| Cooling Ingredient 2 | 0.05 |
| Cooling Ingredient 3 | 0.04 |
| Sorbitol Solution (70%) | 10.00 |
| Hydroxyalkylcellulose | 0.45 |
| Preservative | 0.20 |
| Emulsifier | 0.10 |
| Water | 54.11 |
| Total | 100.00 |

Upon mixing, the compositions should result in a sensation that is warming plus tingling.

EXAMPLE 4

Warming and Flushing Sensation

First and second compositions set forth below may be applied to a first and a second partner as set forth in Examples 1 and 2 above.

| First Composition (Warming) | |
| --- | --- |
| Ingredient | % w/w |
| Propylene Glycol | 25.00 |
| Polyethylene Glycol 400 | 75.00 |
| Total | 100.00 |

| Second Composition (Flushing) | |
| --- | --- |
| Ingredient | % w/w |
| Propylene Glycol | 24.50 |
| Polyethylene Glycol 400 | 75.00 |
| Ginger | 0.50 |
| Total | 100.00 |

Sensation Results:

Both partners should feel warming and flushing.

EXAMPLE 5

Warming and Numbing Sensations

First and second compositions set forth below may be applied to a first and a second partner as set forth in Examples 1 and 2 above.

| First Composition (Warming): | |
| --- | --- |
| Ingredient | % w/w |
| Propylene Glycol | 25.00 |
| Polyethylene Glycol 400 | 75.00 |
| Total | 100.00 |

| Second Composition (Numbing): | |
| --- | --- |
| Ingredient | % w/w |
| Propylene Glycol | 24.50 |
| Polyethylene Glycol 400 | 75.00 |
| Benzocaine | 0.50 |
| Total | 100.00 |

Sensation Results:

Both partners should feel both a warming and a numbing sensation.

EXAMPLE 6

Warming and Irritation Sensation

First and second compositions set forth below may be applied to a first and a second partner as set forth in Examples 1 and 2 above.

| First Composition (Warming): | |
|---|---|
| Ingredient | % w/w |
| Propylene Glycol | 25.00 |
| Polyethylene Glycol 400 | 75.00 |
| Total | 100.00 |

| Second Composition (Irritant): | |
|---|---|
| Ingredient | % w/w |
| Propylene Glycol | 24.50 |
| Polyethylene Glycol 400 | 75.00 |
| Ginger Extract | 0.50 |
| Total | 100.00 |

Sensation Results:

Both partners should feel both a warming and an irritating sensation.

EXAMPLE 7

Warming and Tactile Sensation

First and second compositions set forth below may be applied to a first and a second partner as set forth in Examples 1 and 2 above.

| First Composition (Warming) | |
|---|---|
| Ingredient | % w/w |
| Propylene Glycol | 25.00 |
| Polyethylene Glycol 400 | 75.00 |
| Total | 100.00 |

| Second Composition (Tactile/Frictional) | |
|---|---|
| Ingredient | % w/w |
| Propylene Glycol | 24.50 |
| Polyethylene Glycol 400 | 75.00 |
| Microbeads | 0.50 |
| Total | 100.00 |

Sensation Results:

Both partners should feel a warming sensation and a heightened tactile sense due to friction created with the microbeads.

EXAMPLE 8

Warming and Tingling Sensation

First and second compositions set forth below may be applied to a first and second partner as set forth in Examples 1 and 2 above.

| First Composition (Warming) | |
|---|---|
| Ingredient | % w/w |
| Polyethylene Glycol 400 | 75.00 |
| Propylene glycol | 24.60 |
| DL-a-Tocopherol | 0.10 |
| Hydroxypropyl cellulose | 0.30 |
| Total | 100.00 |

| Second Composition (Tingling) | |
|---|---|
| Ingredient | % w/w |
| Propylene Glycol, USP | 15.00 |
| Natrosol 250H, NF | 0.75 |
| Benzoic Acid, USP | 0.20 |
| Polysorbate 60 | 1.00 |
| Cooling Ingredient 1 | 0.12 |
| Cooling Ingredient 2 | 0.06 |
| Optamint 188526 | 0.06 |
| Purified water | 82.61 |
| pH adjuster | 0.02 |
| Purified water | 0.18 |
| Total | 100.00 |

EXAMPLE 9

Warming and Tingling Sensation

First and second compositions set forth below may be applied to a first and a second partner as set forth in Examples 1 and 2 above.

| First Composition (Warming) | |
|---|---|
| Ingredient | % w/w |
| Glycerin | 56.28 |
| Propylene Glycol | 40.00 |
| Flavor 1 | 2.50 |
| Honey | 1.00 |
| Preservative | 0.20 |
| Flavor 2 | 0.02 |
| Total | 100.00 |

| Second Composition (Tingling) | |
|---|---|
| Ingredient | % w/w |
| Propylene Glycol, USP | 15.00 |
| Natrosol 250H, NF | 0.75 |

-continued

Second Composition (Tingling)

| Ingredient | % w/w |
| --- | --- |
| Benzoic Acid, USP | 0.20 |
| Polysorbate 60 | 1.00 |
| Cooling ingredient 1 | 0.06 |
| Optamint 188526 | 0.06 |
| Purified water I | 82.61 |
| Sodium hydroxide pellet* | 0.02 |
| Purified water II | 0.18 |
| Total | 100.00 |

Upon mixing, the compositions should result in a enhanced sensation that is warming plus tingling.

EXAMPLE 10

The compositions and methods of this invention be used by couples to bring fun, excitement and playfulness to their intimate relationship. They may be characterized as a his/her interactive lubricant. The woman may apply to her skin one of the lubricants and will feel a slight sensation; the man should then apply to his skin another lubricant composition and will feel a slight sensation, when the two meet through intercourse a new and/or more intense warming sensation should be felt. The benefit is the fun and excitement of experiencing a new sensation together and the enhanced pleasure that comes from the warming sensation. Two combination technologies may be exemplified herein as follows:

Warming and tingling lubricants

Improved warming and water base lubricants

It is expected that the combined experience using at least two lubricant compositions should be better than each individual experience, when intercourse begins (penetration) as well as make the overall experience significantly better.

What is claimed is:

1. A method of creating a combined sensation on the skin or mucosa of at least one of at least two individuals comprising:
 a) applying a first topical warming composition comprising at least one polyhydric alcohol to the skin or mucosa of at least a first individual, wherein said first topical warming composition is substantially anhydrous;
 b) applying a second topical composition other than a warming composition to the skin or mucosa of at least a second individual, wherein said second topical composition other than a warming composition is aqueous and different from said first topical composition;
 c) bringing the skin or mucosa of at least the first individual to which said first warming composition is applied into contact with the skin or mucosa of at least the second individual to which said second composition is applied; whereby said first warming and said second topical compositions interact and result in a combined different or intensified sensation in at least one of said individuals.

2. A method according to claim 1 wherein said first warming and said second topical compositions interact to create a combined sensation or intensification thereof in both said first and said second individuals.

3. A method according to claim 1 wherein said second compositions is a lubricating composition.

4. A method according to claim 1 wherein said second topical composition comprises frictional elements.

5. A method according to claim 4 wherein said frictional elements comprise microbeads.

6. A method according to claim 1 wherein said second topical composition comprises a cooling composition.

7. A method according to claim 6 wherein said cooling composition comprises a cooling ingredient selected from the group consisting of menthol, sorbitol, clohexanecarboxamide, N-methyl-5-methyl-2-(1-methylethyl and N,2,3-trimethyl-2-isopropyl butamide.

8. A method according to claim 1 wherein said second topical composition comprises a tingling composition.

9. A method according to claim 8 wherein said tingling composition comprises a tingling ingredient selected from the group consisting of methyl salicylate, methyl nicotinate and menthyl lactate.

10. A method according to claim 1 said second topical composition comprises a numbing composition.

11. A method according to claim 10 wherein said numbing composition comprises an anesthetic ingredient selected from the group consisting of benzocaine, novocaine, lidocaine, tetracaine, lignocaine and mepivacaine.

12. A method according to claim 1 wherein said second topical composition comprises an irritating composition.

13. A method according to claim 12 wherein said irritating composition comprises a pleasantly irritating amount of an irritation ingredient selected from the group consisting of pepper, capsicum, olive, ginger and cloves.

14. A method according to claim 1 wherein at least one of said compositions is a flushing composition.

15. A method according to claim 14 wherein said flushing composition comprises a flushing ingredient selected from the group consisting of pepper, chili pepper and ginger.

16. A method according to claim 1 wherein said first individual applies said first warming composition to said second individual and wherein said second individual applies said second topical composition to said first individual.

* * * * *